United States Patent
Doyle et al.

(10) Patent No.: US 10,111,932 B2
(45) Date of Patent: Oct. 30, 2018

(54) COAGONISTS OF GLUCAGON-LIKE PEPTIDE 1 RECEPTOR AND NEUROPEPTIDE Y2 RECEPTOR

(71) Applicants: Robert Doyle, Manlius, NY (US); Ron Bonaccorso, Syracuse, NY (US)

(72) Inventors: Robert Doyle, Manlius, NY (US); Ron Bonaccorso, Syracuse, NY (US)

(73) Assignee: Syracuse University, Syracuse, NY (US)

(*) Notice: Subject to any disclaimer, the term of this patent is extended or adjusted under 35 U.S.C. 154(b) by 0 days.

(21) Appl. No.: 15/754,386

(22) PCT Filed: Aug. 26, 2016

(86) PCT No.: PCT/US2016/048873
§ 371 (c)(1),
(2) Date: Feb. 22, 2018

(87) PCT Pub. No.: WO2017/035432
PCT Pub. Date: Mar. 2, 2017

(65) Prior Publication Data
US 2018/0271947 A1  Sep. 27, 2018

Related U.S. Application Data

(60) Provisional application No. 62/210,233, filed on Aug. 26, 2015.

(51) Int. Cl.
*A61K 38/00* (2006.01)
*A61K 38/26* (2006.01)
*A61K 38/22* (2006.01)

(52) U.S. Cl.
CPC .......... *A61K 38/26* (2013.01); *A61K 38/2271* (2013.01)

(58) Field of Classification Search
None
See application file for complete search history.

(56) References Cited

U.S. PATENT DOCUMENTS 592,097 A   10/1897  Moebius et al.
8,058,233 B2  11/2011  Cowley et al.

FOREIGN PATENT DOCUMENTS

WO  2014/140113  9/2014

OTHER PUBLICATIONS

Tran et al. Am Health Drug Benefits. 2017;10(4):178-188; www.AHDBonline.com).*
R&D systems; Visited Jul. 5, 2018 https://www.rndsystems.com/search?common_name=NPY%20Receptor%20Agonists.*
Clardy-James et al. "Synthesis, characterization and pharmacodynamics of vitamin-B (12)-conjugated glucagon-like peptide-1," Chem Med Chem. Nov. 30, 2013 (Nov. 30, 2012), vol. 8, pp. 582-586 [pp. 1-13 for citations]. entire document.
Henry et al. "Vitamin B12 conjugation of peptide-YY(3-36) decreases food intake compared to native peptide-YY (3-36) upon subcutaneous administration in male rats," Endocrinology, Feb. 6, 2015 (Feb. 6, 2015), vol. 156, pp. 1739-1749. entire document.
International Search Report Form PCT/ISA/220, International Application No. PCT/US2016/048873, pp. 1-6, dated Nov. 15, 2016.

* cited by examiner

*Primary Examiner* — Jeanette M Lieb
(74) *Attorney, Agent, or Firm* — Bond Schoeneck & King, PLLC; David Nocilly; George McGuire

(57) ABSTRACT

Peptide sequences that can serve as agonists of both the glucagon-like peptide 1 receptor (GLP-IR) and the neuropeptide Y2 receptor (NPYR2). The peptide sequences include regions that correspond to certain aspect of natural substrates and known agonists of the glucagon-like peptide 1 receptor (GLP-IR) and the neuropeptide Y2 receptor (NPYR2) in a single sequence.

14 Claims, 21 Drawing Sheets

Specification includes a Sequence Listing.

| | |
|---|---|
| Ex-4 | HGEGTFTSDLSKQMEEEAVRLFIEWLKNGGPSSGAPPPS-NH2 |
| PYY | IKPEAPREDASPEELNRYYASLRHYLNLVTRQRY-NH2 |
| RLB001 | HGEGTFTSDLSKQMEEEAVRLFIEWLKNGGPSSTRQRY-NH2 |
| RLB002 | HGEGTFTSDLSKQMEEEAVRLFIEWLRHYLNLVTRQRY-NH2 |
| RLB003 | IKPEAPREDASPEELNQAYKFIAYLNLVTRQRY-NH2 |

FIG. 7

| 1 | HGEGTFTSDLSKQMEEEAVRLFIEWLKNGGPSSGTRQRY-NH2 (SEQ ID NO: 6) |
| --- | --- |
| 2 | HGEGTFTSDLSKQMEEEAVRLFIEWLKNGGTRQRY-NH2 (SEQ ID NO: 7) |
| 3 | HGEGTFTSDLSKQMEEEAVRLFIEWLKNGGLRHYLNLVTRQRY-NH2 (SEQ ID NO: 8) |
| 4 | HAEGTFTSDVSSYLEGQAAKEFIAWLVKGRGTRQRY-NH2 (SEQ ID NO: 9) |
| 5 | HGEGTFTSDVSSYLEGQAAKEFIAWLVKGRGTRQRY-NH2 (SEQ ID NO: 10) |
| 6 | HAEGTFTSDVSSYLEGQAAKEFIAWLVKGRGLRHYLNLVTRQRY-NH2 (SEQ ID NO: 11) |
| 7 | HGEGTFTSDVSSYLEGQAAKEFIAWLVKGRGLRHYLNLVTRQRY-NH2 (SEQ ID NO: 12) |
| 8 | HGEGTFTSDLSKQMEEEAVRLFIEWLKNGGPSSGAPPPSTRQRY-NH2 (SEQ ID NO: 13) |
| 9 | HGEGTFTSDLSKQMEEEAVRLFIEWLKNGGPSSGAPPPSLRHYLNLVTRQRY-NH2 (SEQ ID NO: 14) |

FIG. 8

| RLB004 | HGEGTFTSDLSKQMEEEAVRLFIEWLKNGGPSSRHYLNLVTRQRY-NH2 (SEQ ID NO: 15) |
|---|---|
| RLB005 | HGEGTFTSDLSKQMEEEAVRLFIEWLKNGGPSSTRQ-NH2 (SEQ ID NO: 16) |
| RLB006 | HGEGTFTSDLSK(azido)QMEEEAVRLFIEWLKNGGPSSTRQRY-NH2 (SEQ ID NO: 17) |

FIG. 9

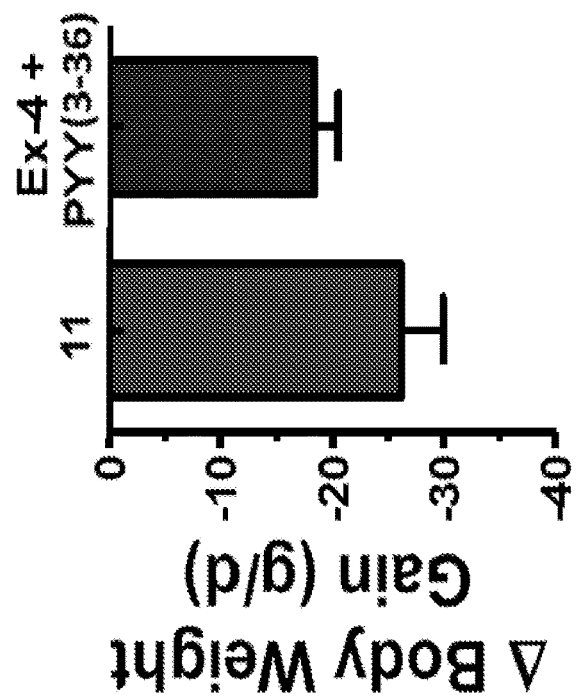
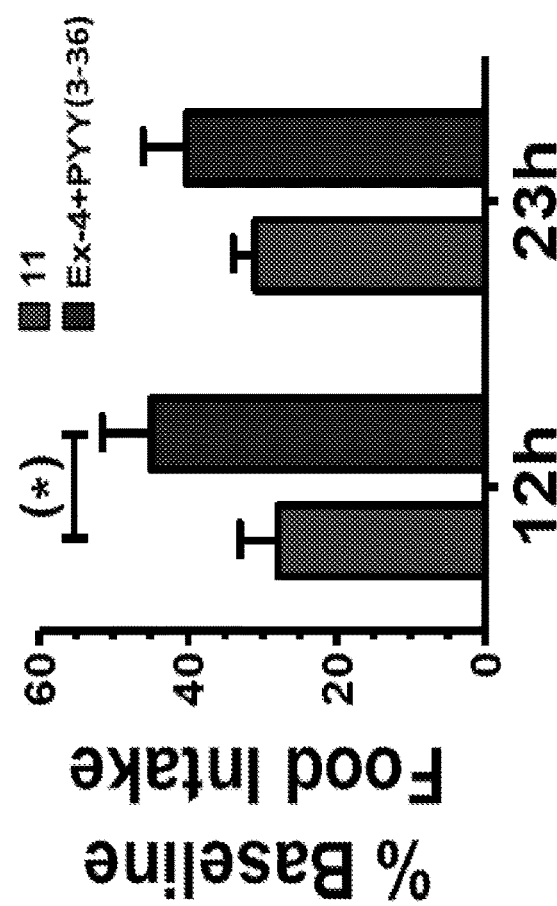
FIG. 18

| Peptide | EC$_{50}$ at Receptors Tested | | | | |
|---|---|---|---|---|---|
| | NPY1 | NPY2 | GLP-1 | GIP | Glugagon |
| PYY(3-36) | >300 nM | 16 nM | NT | NT | NT |
| Ex-4 | >1 µM | >300 nM | 26 pM | >1 µM | >300 nM |
| *(11) | >1 µM | >300 nM | 50 pM | 275 nM | >300 nM |
| (12) | >1 µM | 59 nM | 265 pM | >1 µM | NT |
| (13) | >1 µM | >300 nM | >1 µM | >1 µM | NT |
| *(14) | >1 µM | 107 nM | 97 pM | >1 µM | >300 nM |
| (15) | NT | NT | 44 pM | 173 nM | NT |
| **(16) | NT | NT | 127 pM | NT | NT |

FIG. 21

COAGONISTS OF GLUCAGON-LIKE PEPTIDE 1 RECEPTOR AND NEUROPEPTIDE Y2 RECEPTOR

CROSS-REFERENCE TO RELATED APPLICATION

The present application claims priority to U.S. Provisional No. 62/210,233 filed on Aug. 26, 2015.

BACKGROUND OF THE INVENTION

1. Field of the Invention

The present invention relates to peptides for treating weight loss and glucose levels and, more specifically, to a single peptide that can trigger weight loss while controlling glucose levels.

2. Description of the Related Art

The glucagon-like peptide 1 receptor (GLP-1R) is involved in stimulating the release of insulin in a glucose dependent manner. As a result, GLP-1R agonists have been the source of development for drugs that can be used to treat insulin deficiency diseases such as diabetes. The neuropeptide Y2 receptor (NPYR2) is involved in appetite signaling and suppression. Accordingly, there is a need in the art for a drug that could serve as an agonist of both receptors, thereby more fully addressing the problems associated with glucose regulation and food intake.

BRIEF SUMMARY OF THE INVENTION

The present invention comprises peptide sequences that can serve as agonists of both the glucagon-like peptide 1 receptor (GLP-1R) and the neuropeptide Y2 receptor (NPYR2). In particular, the invention comprises certain non-naturally occurring peptides that can successfully serve as agonists for both receptors. The present invention may also be used as a coagonist at other receptors, such as the NPYR1 or NPYR4 or NPYR5, and not necessarily exclusively GLP-1R and NPYR2.

BRIEF DESCRIPTION OF THE SEVERAL VIEWS OF THE DRAWING(S)

The present invention will be more fully understood and appreciated by reading the following Detailed Description in conjunction with the accompanying drawings, in which:

FIG. 7 is a chart of a comparison of Ex-4 and PYY along with exemplary peptides according to the present invention highlighting the critical components of each;

FIG. 8 shows potential variations of RLB001 that may have comparable or better function at both the GLP-1R and NPYR2;

FIG. 9 is a table of additional sequences according to the present invention;

FIG. 18 is a graph of on the left is shown food intake over a two day study with DIO rats administered either 2.4 nmol/kg of Peptide 11 or an equimolar mixture of Ex-4 and PYY(3-36), and on the right is shown the change in body weight gain of the Peptide 11 treatment vs the equimolar Ex-4 and PYY(3-36).

FIG. 21 is a table of additional sequences according to the present invention.

DETAILED DESCRIPTION OF THE INVENTION

Figures 1A, 1B:
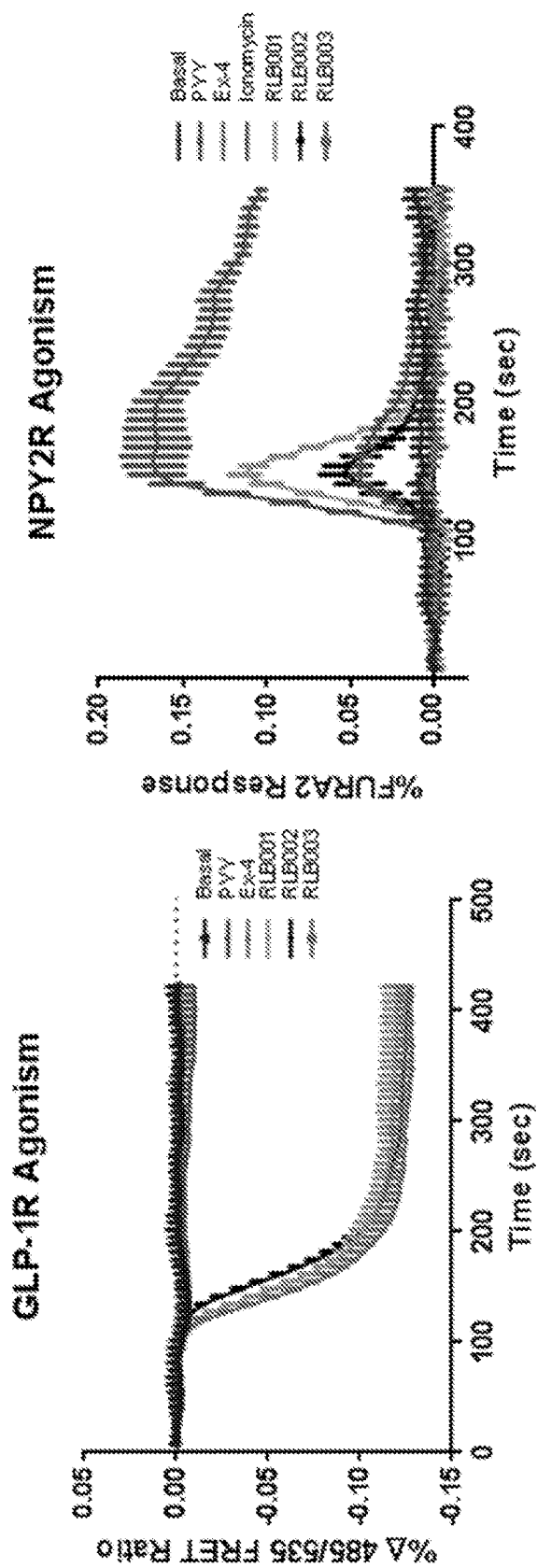
FIGS. 1A and 1B are graphs of the results of agonism screening for certain peptides according to the present invention.

Referring now to the drawings, wherein like reference numerals refer to like parts throughout, the present inventions comprises peptide sequences that are coagonists of GLP-1R and NPYR2. The sequences of the present invention were designed by combining certain aspects of the natural substrates or known agonists of GLP-1R and NPYR2, such as Peptide YY (IKPEAPREDASPEELN-RYYASLRHYLNLVTRQRY-NH2; SEQ ID NO: 1) and exendin-4 (HGEGTFTSDLSKQMEEEAVRLFIEWLKNG-GPSSGAPPPS-NH2; SEQ. ID NO: 2).

Example 1

Following the approach of the present invention, the sequences HGEGTFTSDLSKQMEEEAVRLFIEWLKNG-GPSSTRQRY-NH2 (SEQ ID NO: 3), referred to herein as Peptide RLB001, HGEGTFTSDLSKQMEEEAVR-LFIEWLRHYLNLVTRQRY-NH2 (SEQ ID NO: 4), referred to herein as Peptide RLB002, and IKPEAPRE-DASPEEENQAYKEFIAYLNLVTRQRY-NH2 (SEQ ID NO: 5), referred to herein as Peptide RLB003 were designed and synthesized through solid phase peptide synthesis.

Referring to FIGS. 1A and 1B, the sequences were screened for agonism with respect to each of GLP-1R and NPYR2 by performing a either a Fluorescence Resonance Energy Transfer (FRET) assay to show GLP-1R agonism or following the fluorescence of FURA 2 upon calcium release to show NPYR2 agonism and plotting the change in either FRET or fluorescence over a predetermined time period. These assays have been used previously to show function at each receptor respectively. The peptides synthesized according to the present invention were compared against a basal measurement, exendin-4 (a known agonist of GLP-1R), Peptide YY (a known agonist of NPYR2), and ionomycin.

Figures 2A, 2B:
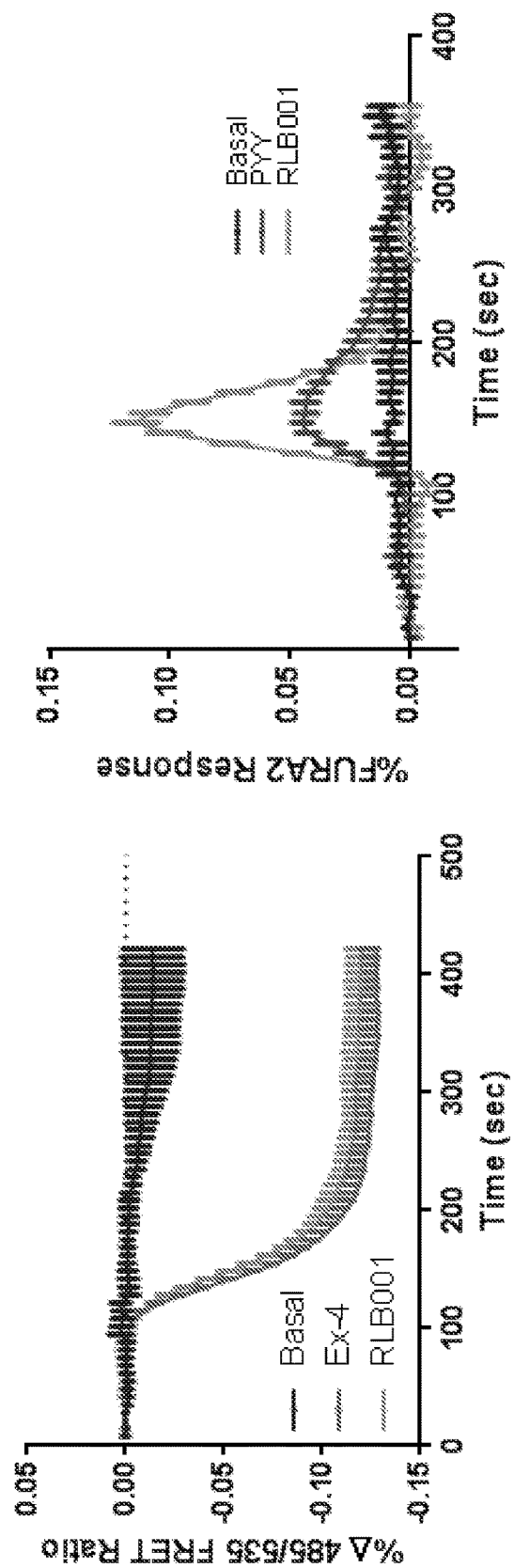
FIGS. 2A and 2B are graphs of the results of agonism screening for certain peptides according to the present invention.
Figure 3:
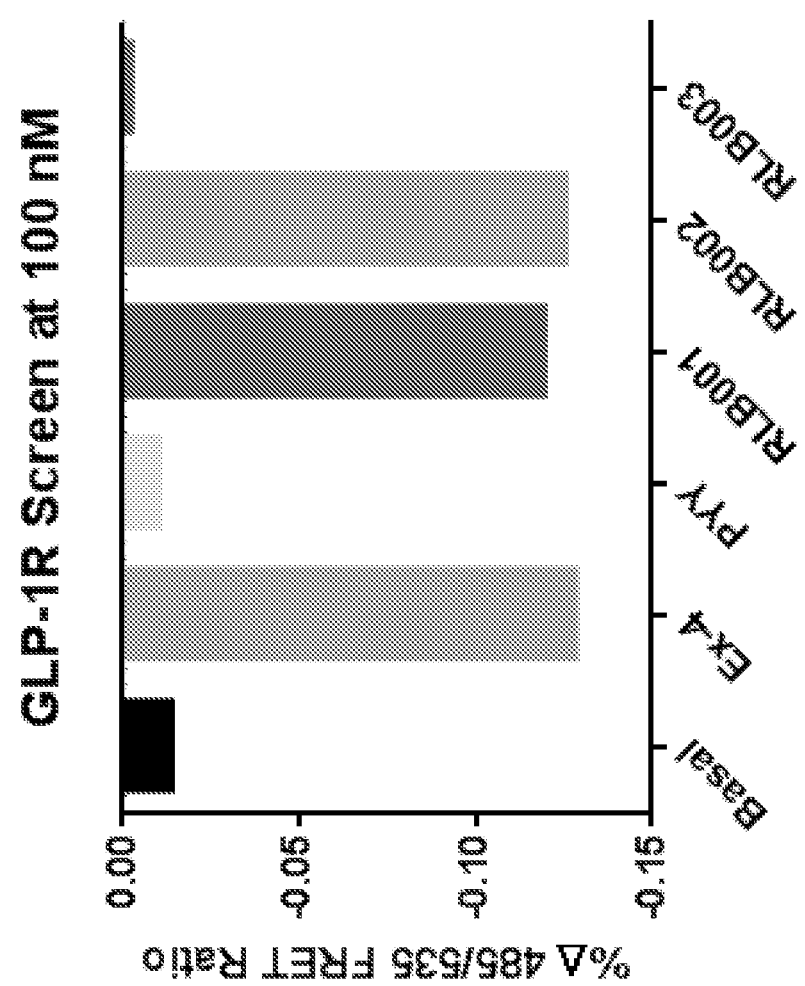
FIG. 3 is a chart of GLP-1R agonism screening for certain peptides at a concentration of 100 nM.
Figure 4:
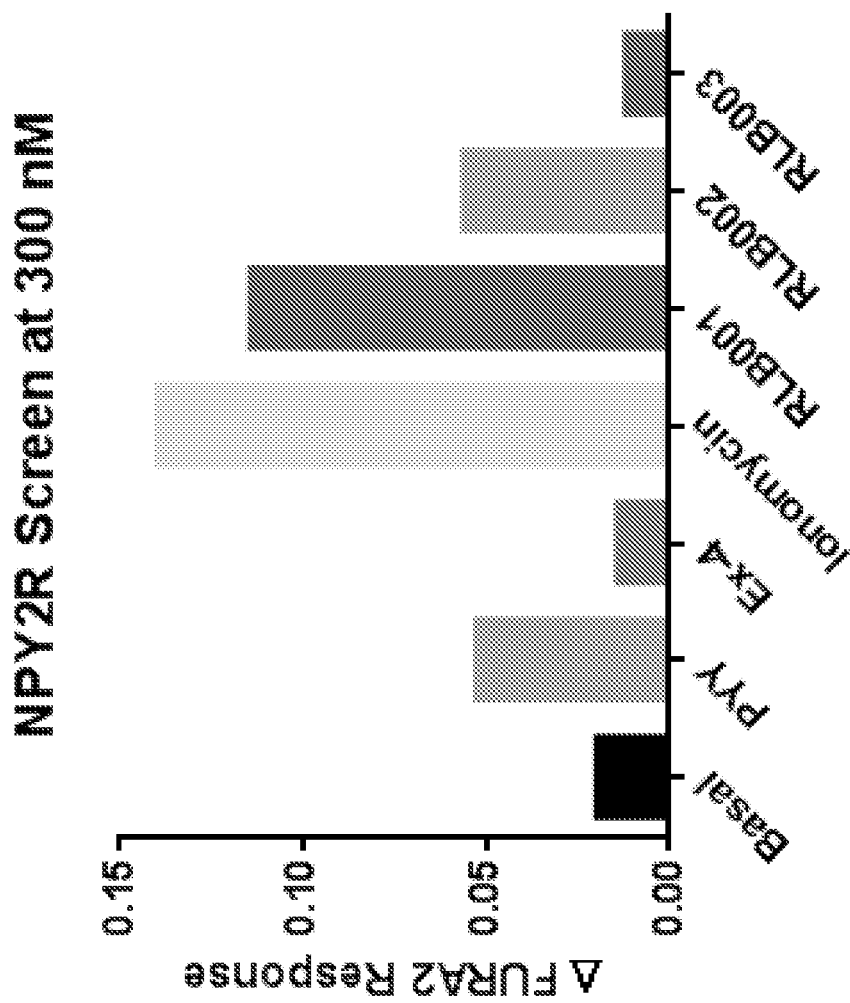
FIG. 4 is a chart of NPYR2 agonism screening for certain peptides at a concentration of 100 nM.
Figure 5:
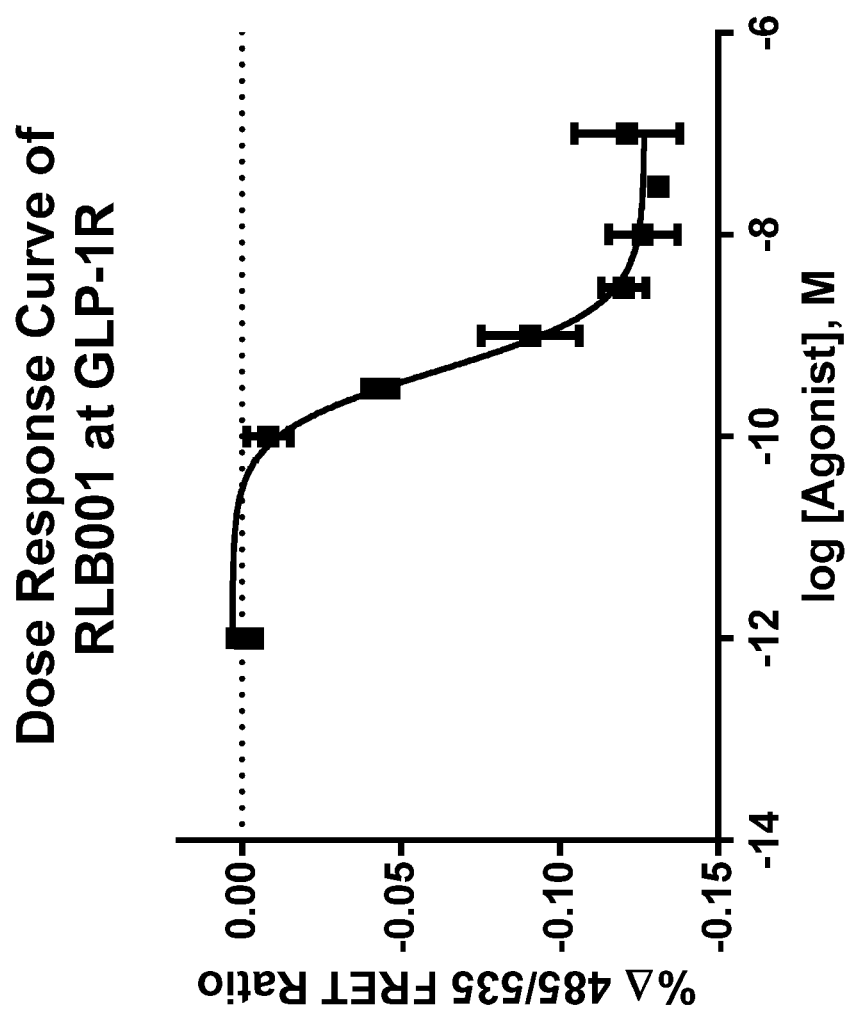
FIG. 5 is a graph of GLP-1R agonism of an exemplary peptide according to the present invention.
Figure 6:
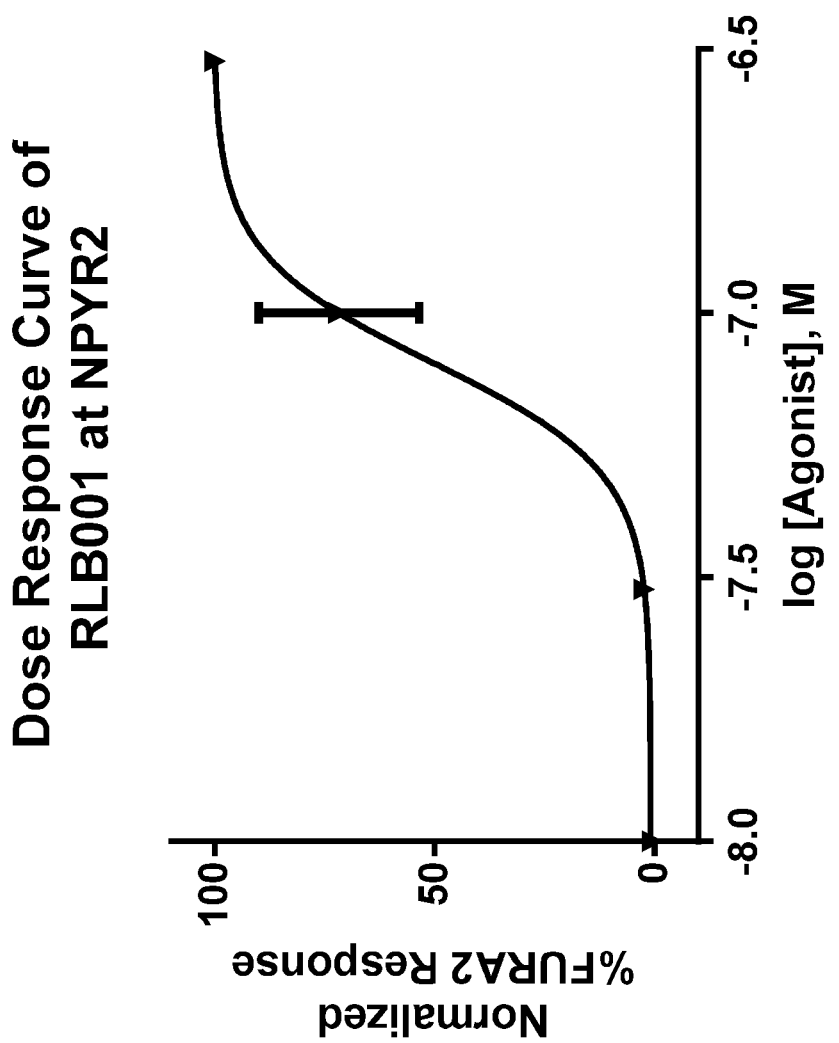
FIG. 6 is a graph of NPYR2 agonism of an exemplary peptide according to the present invention.

Referring to FIGS. 2A and 2B, Peptide RLB001 was screened for agonism with respect to each of GLP-1R and NPYR2, as well as the controls discussed above. Referring to FIG. 3, screening of the peptides for GLP-1R agonism revealed that RLB001 and RLB002 were effective agonists. Referring to FIG. 4, screening of the peptides for NPYR2 agonism revealed that RLB001 was even more effective that known agonists of NPYR2, such as PYY. As seen in FIG. 5, Peptide RLB001 done in triplicate has an $EC_{50}$ of 50 pM at GLP-1R. As seen in FIG. 6, Peptide RLB001 done in duplicate has an $EC_{50}$ of 81 nM at NPYR2. The relevant portions of PYY and exendin-4 used as a basis for forming the sequences according to the present invention are seen in FIG. 7. Referring to FIG. 8, SEQ ID NO. 6 through SEQ ID NO. 14 represent variations of RLB001 that may have comparable or better function at both the GLP-1R and NPYR2 and may be readily tested as described above to confirm their efficacy. The present invention may also be used as a coagonist at other receptors, such as the NPYR1 or NPYR4 or NPYR5, and not necessarily exclusively GLP-1R and NPYR2.

These results demonstrate that the peptide RLB001 has comparable function at the GLP-1R and the NPYR2. A single peptide may thus be used to activate two receptors responsible for glucose control and appetite suppression. In addition, the unique profile of calcium release after activation at the NPYR2 may indicate biased agonism.

Example 2

To overcome the compensatory effects of PYY(3-36) a hybrid peptide made from fragments of Ex-4 and PYY(3-36) should be able to target both GLP-1R and NPYR2 without the PD effects of two different drugs. The initial series of three sequences were designed with the first two peptides composed primarily of Ex-4 sequence and the third as a modified version of PYY(3-36) to screen for dual agonism. After the results of these three peptides as described above, an additional three sequences were designed, i.e., Peptides RLB004 (HGEGTFTSDLSKQMEEEAVRLFIEWLKNG-GPSSRHYLNLVTRQRY-NH2; SEQ ID NO: 15), RLB005 (HGEGTFTSDLSKQMEEEAVRLFIEWLKNG-GPSSTRQ-NH2; SEQ ID NO: 16), and RLB006 (HGEGT-FTSDLSK(azido)QMEEEAVRLFIEWLKNG-GPSSTRQRY; SEQ ID NO: 17), as seen in FIG. 9, to improve upon the initial series of Peptides RLB001, RLB002, and RLB003 and to produce an effective dual or even triagonist.

In Vitro Screening and Testing

The RLB series peptides were tested for function at receptors corresponding to the glucagon super family of receptors and NPY receptors. These receptors were transfected into either HEK293 cells or CHO cells. HEK 293 cells stably transfected with either GLP-1R or GIPR followed by an infection of adenovirus incorporating AKAR3 to indirectly follow cAMP production. CHO cells were transfected with NPY2R and a promiscuous g protein using FURA2 to follow calcium release.

Screening the RLB Series for GLP-1R Agonism and Dose Response

Function was first established at the GLP-1R by screening the initial conjugates in the HEK-GLP-1R cells. These cells were treated with adenovirus containing AKAR3 and a agonism was determined by a decrease in FRET ratio. The initial screen of compounds is found in FIG. 10 and shows that Peptides 11, 12 and 14 have agonism at the GLP-1R. Peptides 13 showed no function at the GLP-1R at 300 nM making ineffective as a GLP-1R and NPY2R coagonist.

Figure 10:
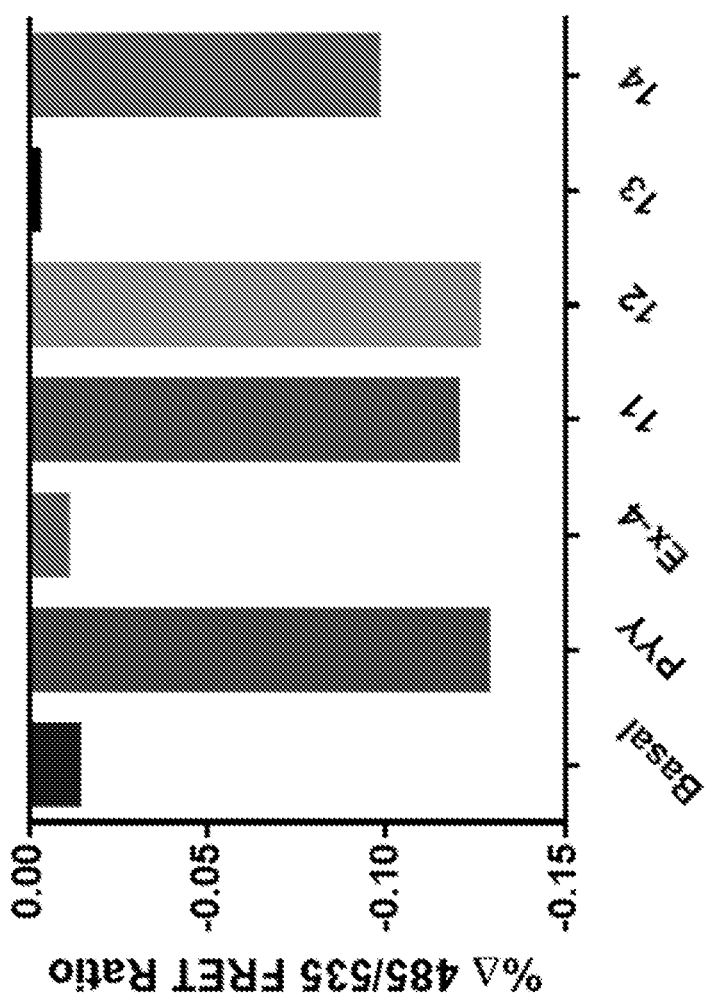
FIG. 10 is a graph of a screen of RLB series peptides at the GLP-1R at 300 nM.
Figure 11:
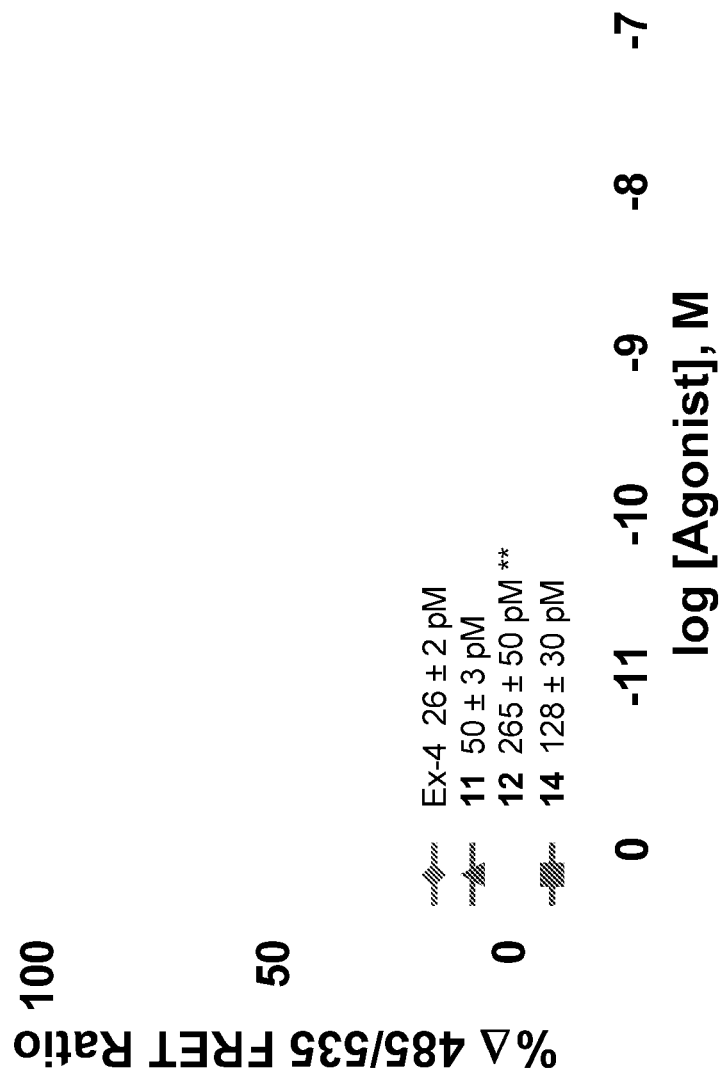
FIG. 11 is a graph of a dose response comparison of Peptides 11, 12 and 14 to Ex-4. 12 has a p-value of 0.0032 compared to Ex-4 and Peptide 11.
Figure 12:
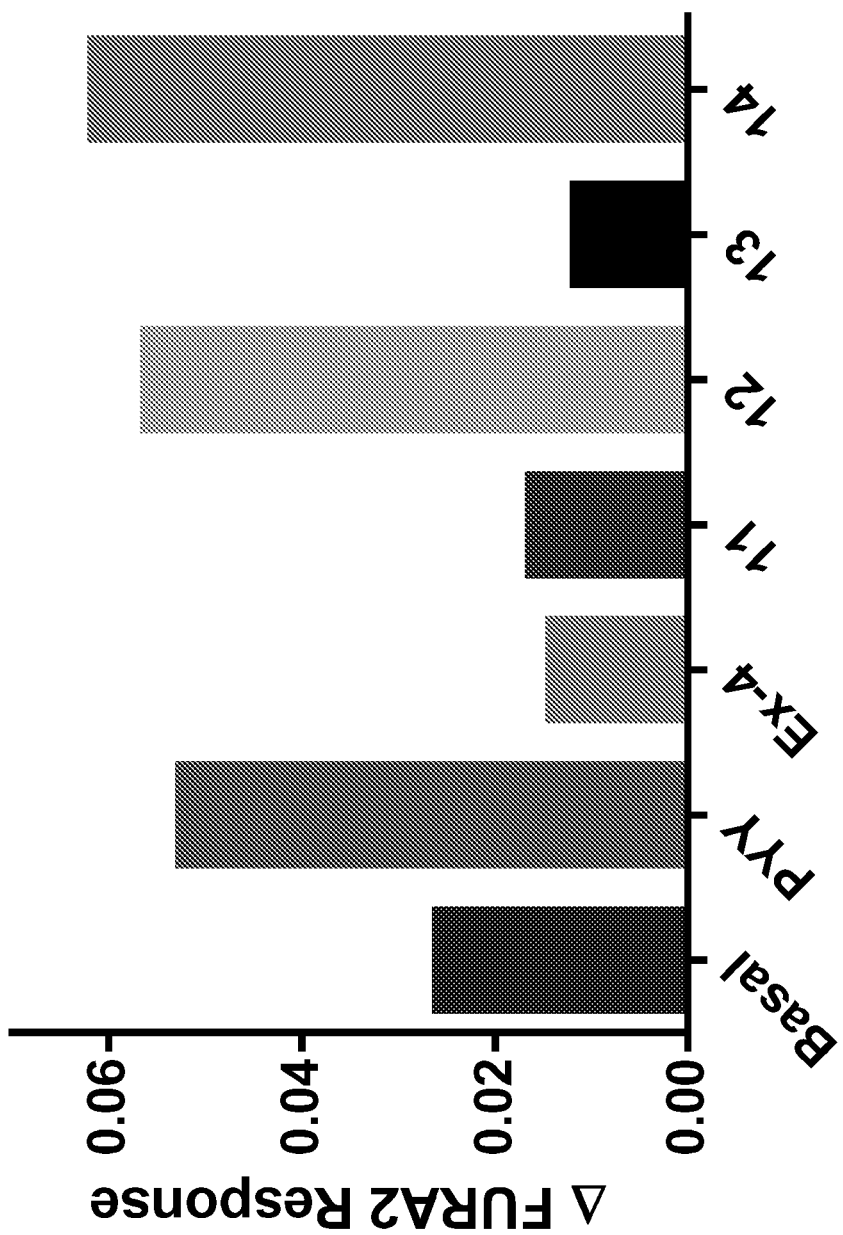
FIG. 12 is a graph of a NPY2R screen with RLB series of peptides at [300 nM]

The initial screen showed that modifications to Ex-4 do not completely hinder function at the GLP-1R. The peptides showing function at the GLP-1R were then analyzed further to establish an $EC_{50}$. FIG. 10 shows that Peptides 11 and 14 are the most effective with $EC_{50}$ values of 50±3 pM and 128±30 pM, respectively and followed by Peptides 12 at 253±50 pM.

Peptides 11, 12 and 14 all retained picomolar agonism at GLP-1R warranting further analysis at NPY2R and other glucagon superfamily receptors. Peptides 13 was discarded as a potential dual agonist due to its loss of function.

Screening the RLB Series for NPY2R Agonism and Dose Response

Figure 13:
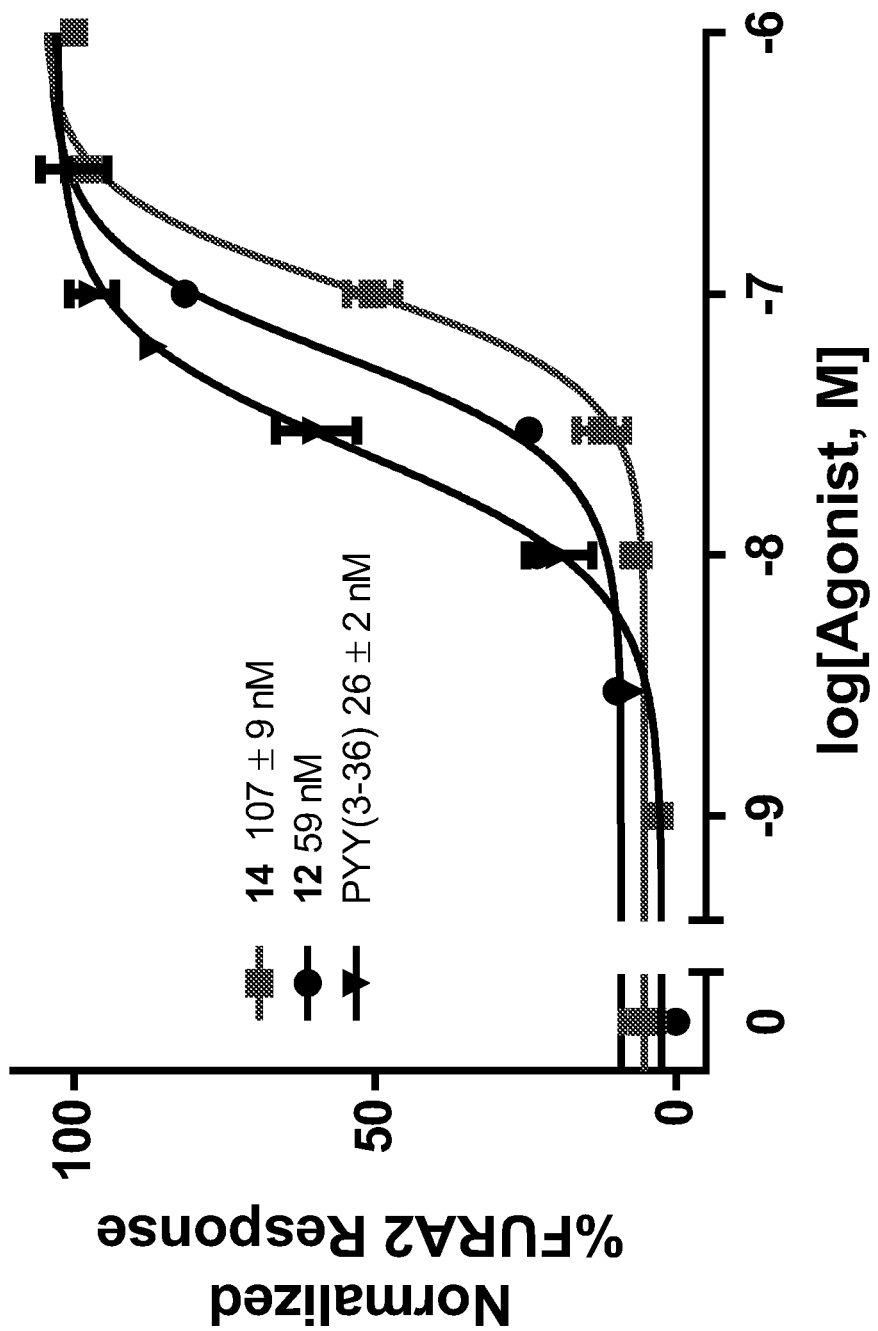
FIG. 13 is a graph of a NPY2R $EC_{50}$s of 12, 59 nM, and 14, 107 nM.

Following a screen at the GLP-1R, a screen for agonism at NPY2R was conducted. FIG. 13 shows full function was only achieved with Peptides 12 and 14. Positive results show that a successful in vitro dual agonist of GLP-1R and NPY2R was achieved.

Figure 14:
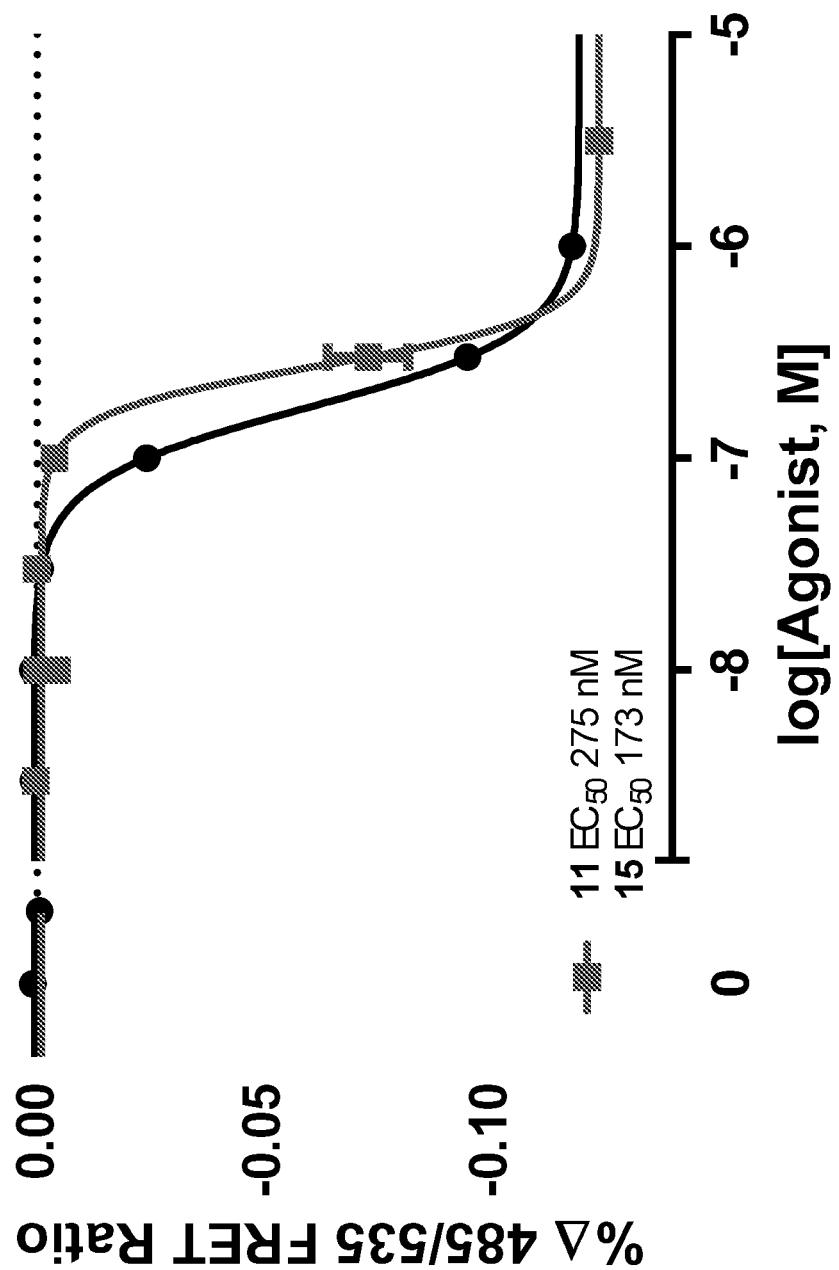
FIG. 14 is a GIPR dose response and $EC_{50}$ values of Peptide 11 (275 nM) and Peptide 15 (173 nM). Note: Ex-4, 12, 14 and PYY were all tested with no agonsim up to 1 µM.

Peptides 12 and 14 were followed up with a full dose response curve to show and $EC_{50}$ for each peptide (see FIG. 13). PYY(3-36) was used as the positive control to show that each peptide shows comparable agonism at the NPY2R through in vitro trials. Peptides 14 had an $EC_{50}$ of 107±9 nM and Peptides 12 had an $EC_{50}$ of 59 nM. Screening the RLB series for GIPR and GCGR agonism and dose response After establishing agonism at the GLP-1R, the RLB series peptides were tested against similar receptors. Receptors in the glucagon receptor superfamily were tested based on the similarities of native peptide agonists. Shown in FIG. 14 are the results of the GIPR screen, where only Peptides 11 and 15 showed any function at the GIPR and Ex-4, PYY, Peptides 12 and 14 showed no function under 1 μM.

Peptides 11 and 14 were screened for gcgr agonism compared to Ex-4. Each of these peptides, including Ex-4, showed slight agonism at the receptor at high concentrations (>300 nM). Only peptides 11, 14 and 14 were confirmed to have function at more than one receptor. Peptides 11 is an effective in vitro dual agonist of GLP-1R and GIPR and Peptides 12 and 14 are effective agonists of GLP-1R and NPY2R.

In Vivo Testing of 11 Compared to Ex-4 and PYY(3-36)

Figure 15:
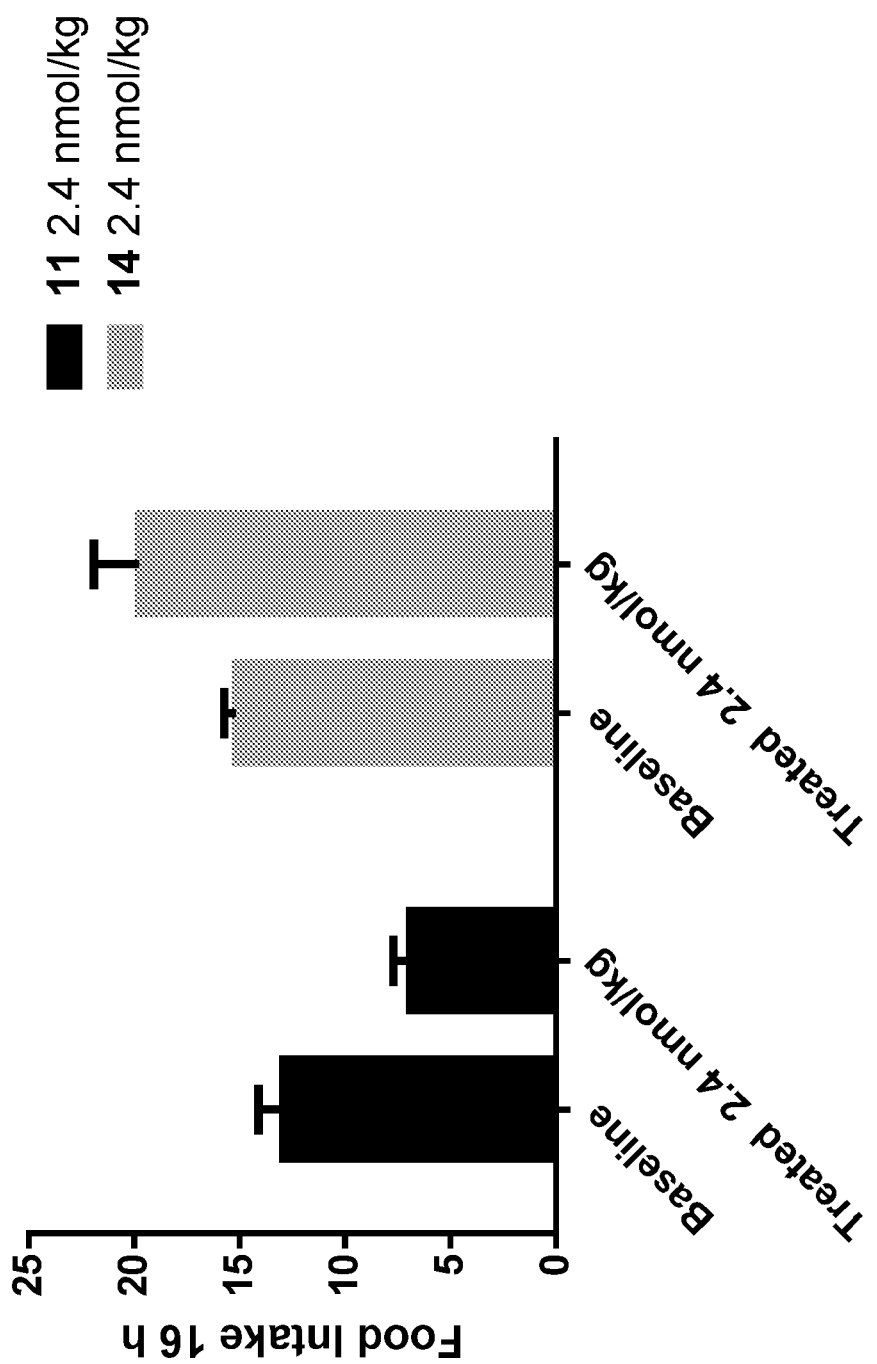
FIG. 15 is a graph of an initial screen of food intake for Peptides 11 and 14 at 2.4 nmol/kg over 16 h.

After the initial screening of the RLB series peptides an in vivo study was planned to compare the dual agonists Peptides 11 and 14 to Ex-4 and PYY(3-36). Since RLB002 was significant less potent at the GLP-1R it was not selected for in vivo testing. A one-day food intake screen of Peptides 11 and 14 showed that Peptide 11 had a reduction in food intake but Peptides 14 actually resulted in the opposite effect and caused an increased food intake from the rats (see FIG. 15). Given the initial results only Peptides 11 was pursued.

Peptide 11 was isolated as the lead candidate for both blood glucose control and weight loss. A dose response study was then done to determine the optimal concentration of Peptide 11.

Figure 16:
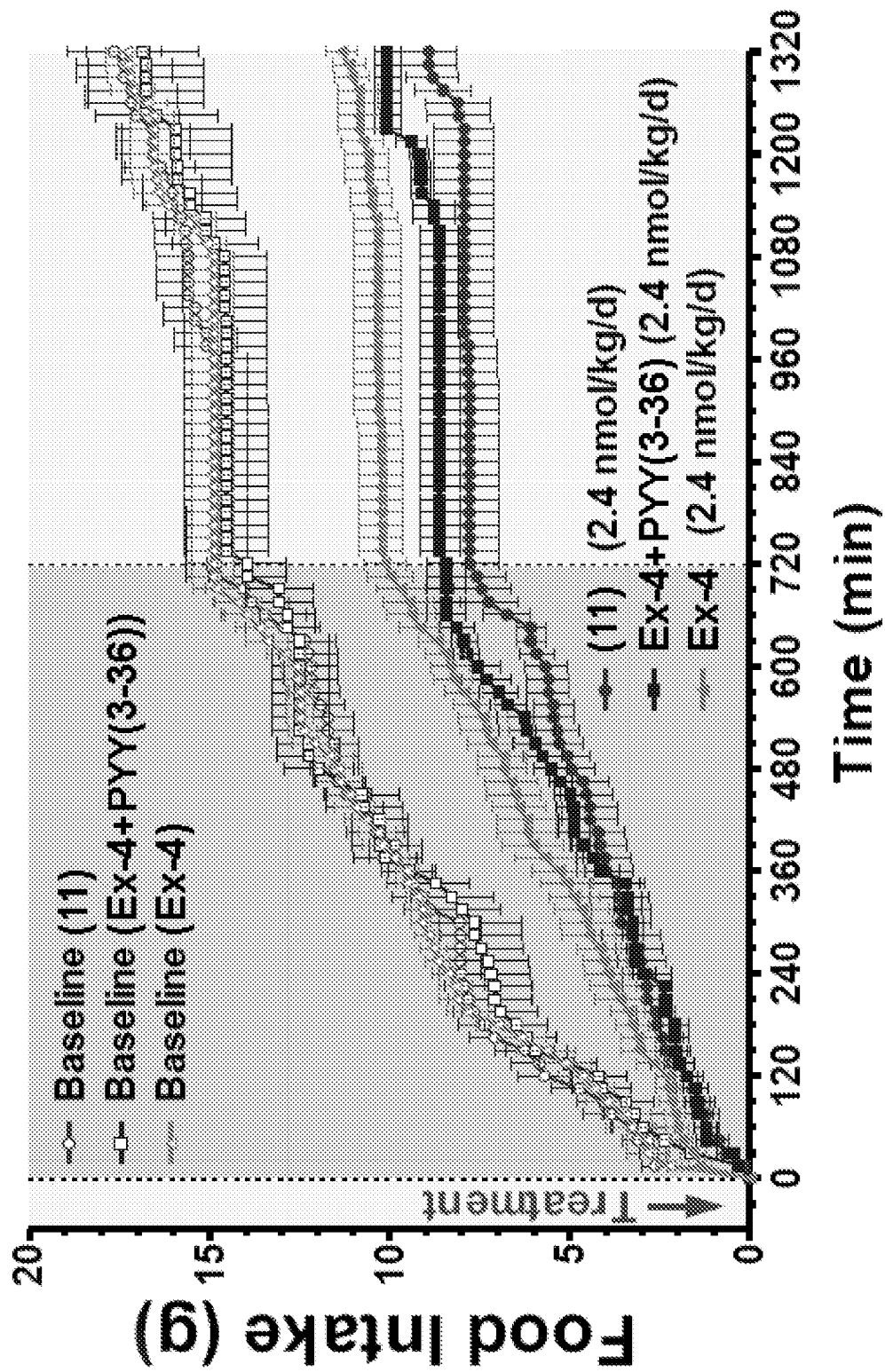
FIG. 16 is a graph of inhibition of food intake of Peptide 11 compared to Ex-4 and Ex-4 and PYY(3-36) combined each at 2.4 nmol/kg/d.
Figure 17:
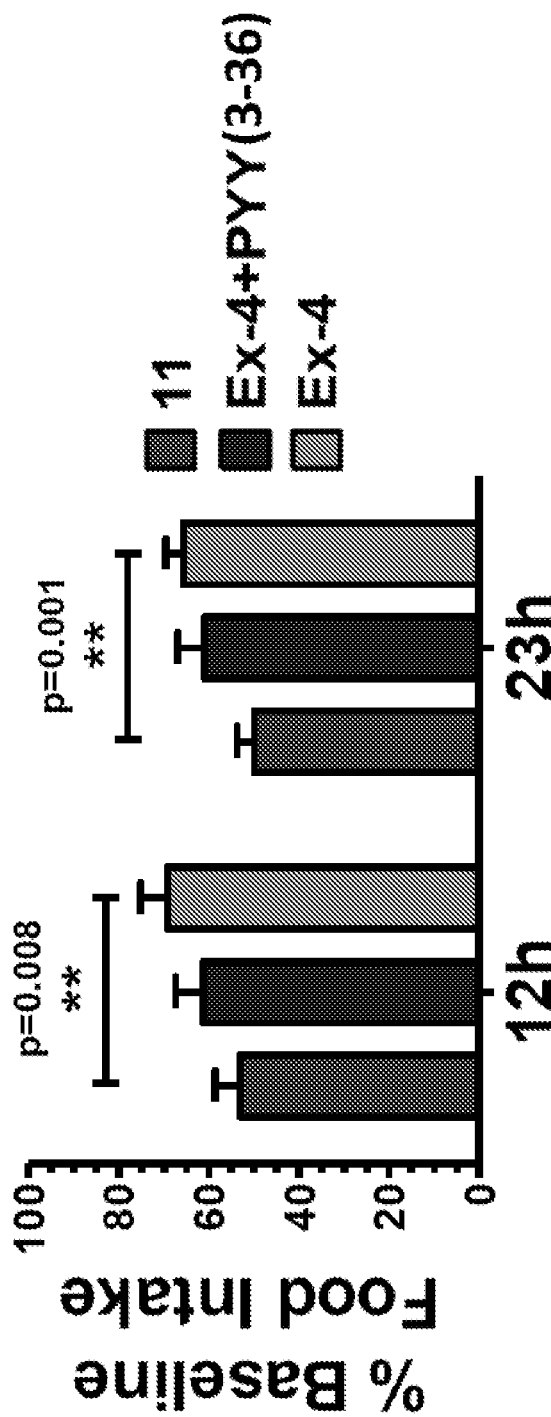
FIG. 17 is a graph of normalized food intake against baseline levels for Peptide 11, Ex-4 and Ex-4 and PYY(3-36) shown over 12 and 23 h.

A two day food intake study was conducted to verify that Peptide 11 behaved uniquely when compared to Ex-4 and co-administration of both Ex-4 and PYY(3-36). FIG. 16 shows the results of a 2 day food intake study comparing Peptide 11, Ex-4 and a mixture of Ex-4 and PYY(3-36) all at 2.4 nmol/kg per day. The total reduction of food intake for all three samples is shown in FIG. 17. Peptide 11 shows a significant improvement over Ex-4 alone and an average lower food intake when compared to Ex-4 and PYY(3-36) co-administration. This establishes that Peptide 11 is not Ex-4 but rather a new and different drug.

Food intake was studied further in diet induced obese (DIO) rats over two days comparing Peptide 11 treatment at 2.4 nmol/kg to an equimolar mixture of Ex-4 and PYY(3-36) at 2.4 nmol/kg (shown in FIG. 18). In each category Peptide 11 is out-performing Ex-4 and PYY(3-36) combination treatments.

Figure 19:
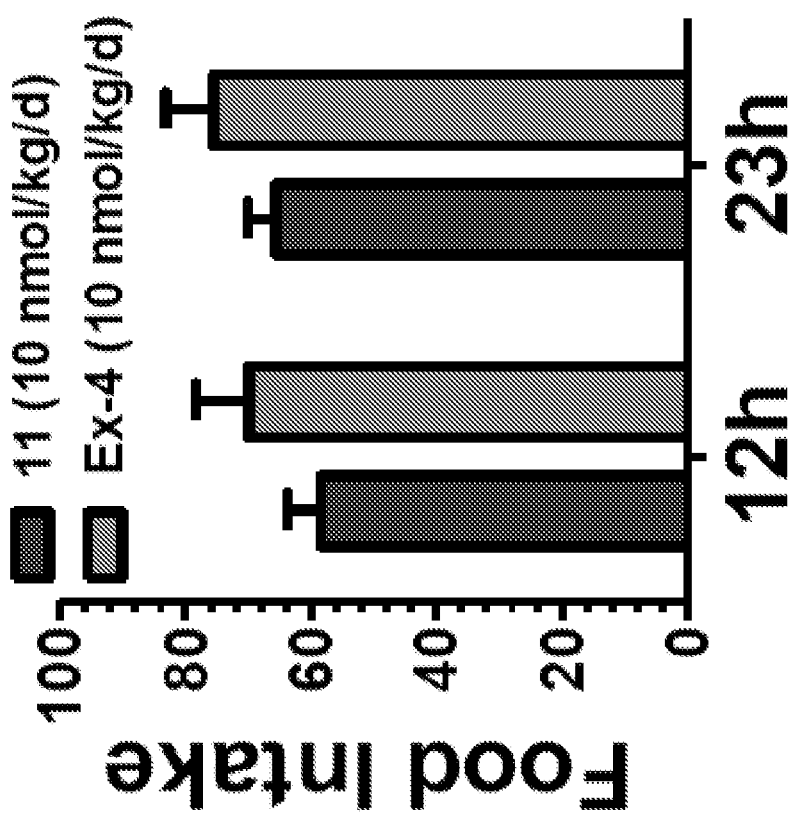
FIG. 19 is a graph of food intake comparison for Peptide 11 and Ex-4 at 10 nmol/kg/d over two days normalized to pretreatment baseline in young 9 week old rats (3 males and 2 females per group)

Direct comparison of Peptide 11 and Ex-4 at 10 nmol/kg dosing is seen in FIG. 19. Peptide 11 is able to provide an average decrease in food intake lower than Ex-4 at both 12 h and 23 h time points.

Glucoregulatory Effects of Peptide 11 Versus Ex-4

Figure 20:
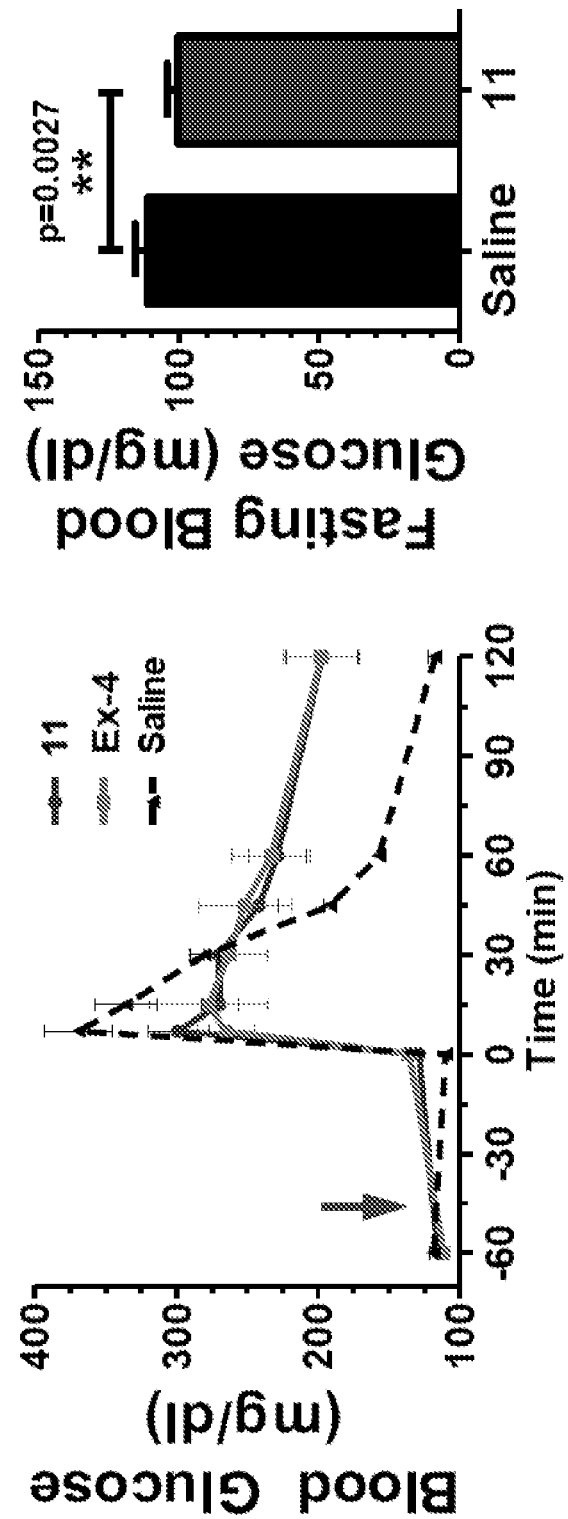
FIG. 20 is a graph of blood glucose levels after administration of saline, Peptide 11 and Ex-4 following a 10 d treatment (10 nmol/kg/d, 2 males and 2 females per group). (Right) Fasting glucose level reduction after a two day treatment with 10 nmol/kg/d 11 in 31-wk old male rats.

Peptide 11 was compared directly to Ex-4 to determine efficacy in blood glucose control. An intraperitoneal glucose tolerance test was performed on rats to treated with Peptide 11, Ex-4 and saline (see FIG. 20). Both Ex-4 and Peptide 11 showed a similar prolonged increase in glucose levels characteristic of Ex-4 in rats. This indicates that the mechanism of action for Peptide 11 to control glucose is the same as Ex-4.

Outcomes and Conclusions

A summary of the results from the in vitro agonism of each receptor is highlighted in FIG. 21. In vitro results were able to confirm dual agonist function with Peptides 11 at the GLP-1R and GIPR and dual agonist function with peptides 12 and 14 at the GLP-1R and NPY2R. Peptides 11 and 14 were the most potent GLP-1R agonist in vitro and were initially chosen for in vivo trials. No peptide showed any significant function at the NPY1R or the glucagon receptor.

Sequences according to the present invention may be further modified according to known processes, such as glycosylation, to improve the use of the sequences as pharmaceuticals by assisting with the delivery of the protein to a subject. For example, N-linked glycosylation may be used to attach oligosaccharides to a nitrogen atom, such as the N4 of asparagine residues. Similarly, O-linked glycosylation may be used to attach glycans to serine and threonine and C-linked glycosylation used for the covalent attachment of a mannose residue to a tryptophan residue.

Sequences according to the present invention may be further modified by pegylation, which is the attachment of a therapeutic protein to poly(ethylene glycol) polymer chains (PEG). The attachment of poly(ethylene glycol) chains can prevent degradation by proteolytic enzymes, reduce rapid clearance of the sequences by the kidneys, and increase the circulating half-life. As is known in the art, PEG is linked to a protein sequence through reactive molecular groups on amino acid side chains such as lysine.

Sequences according to the present invention may be further modified by lipidation. The presence of a lipid group in peptides modulates their hydrophobicity, secondary structures and self-assembling propensities while retaining their abilities to bind to target receptors. Lipidation improves metabolic stability, membrane permeability, bioavailability, and changes pharmacokinetic and pharmacodynamic properties of peptides.

The sequences may also be encapsulated in a suitable vehicle to either aid in the delivery of the compound to target cells, to increase the stability of the composition, or to minimize potential toxicity of the composition. For example, nanoparticles, liposomes, microemulsions, micelles, dendrimers and other phospholipid-containing systems may be used as is known in the art.

Sequences according to the present invention may further be conjugated to known conjugation partners to assist in the use of the sequences as a pharmaceutical. For example, conjugation partners such as an organic drug molecule, an enzyme label, a toxin, a cytostatic agent, a label which can be photoactivated and which is suitable in photodynamic therapy, a pharmaceutically suitable radioactive label, a hapten, digoxigenin, biotin, a chemotherapeutic metal complex or metal, colloidal gold, or a moiety that extends the serum half-life may be used to assist with the delivery of the present invention.

The present invention includes pharmaceutical compositions comprising a preparation of the sequences of the invention. Such pharmaceutical compositions may be for administration for injection, or for oral, nasal, transdermal or other forms of administration, including, e.g., by intravenous, intradermal, intramuscular, intramammary, intraperitoneal, intrathecal, intraocular, retrobulbar, intrapulmonary (e.g., aerosolized drugs) or subcutaneous injection (including depot administration for long term release); by sublingual, anal, vaginal, or by surgical implantation. The treatment may consist of a single dose or a plurality of doses over a period of time. In general, pharmaceutical compositions comprising effective amounts of a sequence according to the invention, whether modified as described above or not, together with pharmaceutically acceptable diluents, preservatives, solubilizers, emulsifiers, adjuvants and/or carriers. Such compositions include diluents of various buffer content, pH and ionic strength; additives such as detergents and solubilizing agents, anti-oxidants, preservatives and bulking substances. The pharmaceutical compositions optionally may include still other pharmaceutically acceptable liquid, semisolid, or solid diluents that serve as pharmaceutical vehicles, excipients, or media. Such compositions may influence the physical state, stability, rate of in vivo release, and rate of in vivo clearance of the present proteins and derivatives. The compositions may be prepared in liquid form, or may be in dried powder, such as lyophilized form. Implantable sustained release formulations are also contemplated, as are transdermal formulations.

What is claimed is:

1. A composition for simultaneously treating obesity and insulin deficiency, comprising a peptide sequence selected from the group consisting of HGEGTFTSDLSKQMEEEAVRLFIEWLKNGGPSSTRQRY-NH2 (SEQ ID NO: 3), HGEGTFTSDLSKQMEEEAVRLFIEWLRHYLNLVTRQRY-NH2 (SEQ ID NO: 4), IKPEAPREDASPEEENQAYKEFIAYLNLVTRQRY-NH2 (SEQ ID NO: 5), HGEGTFTSDLSKQMEEEAVRLFIEWLKNGGPSSRHYLNLVTRQRY-NH2 (SEQ ID NO: 15), HGEGTFTSDLSKQMEEEAVRLFIEWLKNGGPSSTRQ-NH2 (SEQ ID NO: 16), and HGEGTFTSDLSK(azido)QMEEEAVRLFIEWLKNGGPSSTRQRY (SEQ ID NO: 17).

2. The composition of claim 1, wherein the sequence comprises HGEGTFTSDLSKQMEEEAVRLFIEWLKNGGPSSTRQRY-NH2 (SEQ ID NO: 3).

3. The composition of claim 1, wherein the sequence comprises HGEGTFTSDLSKQMEEEAVRLFIEWLRHYLNLVTRQRY-NH2 (SEQ ID NO: 4).

4. The composition of claim 1, wherein the sequence comprises IKPEAPREDASPEEENQAYKEFIAYLNLVTRQRY-NH2 (SEQ ID NO: 5).

5. The composition of claim 1, wherein the sequence comprises HGEGTFTSDLSKQMEEEAVRLFIEWLKNGGPSSRHYLNLVTRQRY-NH2 (SEQ ID NO: 15).

6. The composition of claim 1, wherein the sequence comprises HGEGTFTSDLSKQMEEEAVRLFIEWLKNGGPSSTRQ-NH2 (SEQ ID NO: 16).

7. The composition of claim 1, wherein the sequence comprises HGEGTFTSDLSK(azido)QMEEEAVRLFIEWLKNGGPSSTRQRY (SEQ ID NO: 17).

8. A method of simultaneously treating obesity and insulin deficiency, comprising the steps of administering a peptide sequence selected from the group consisting of HGEGTFTSDLSKQMEEEAVRLFIEWLKNGGPSSTRQRY-NH2 (SEQ ID NO: 3), HGEGTFTSDLSKQMEEEAVRLFIEWLRHYLNLVTRQRY-NH2 (SEQ ID NO: 4), IKPEAPREDASPEEENQAYKEFIAYLNLVTRQRY-NH2 (SEQ ID NO: 5), HGEGTFTSDLSKQMEEEAVRLFIEWLKNGGPSSRHYLNLVTRQRY-NH2 (SEQ ID NO: 15), HGEGTFTSDLSKQMEEEAVRLFIEWLKNGGPSSTRQ-NH2 (SEQ ID NO: 16), and HGEGTFTSDLSK(azido)QMEEEAVRLFIEWLKNGGPSSTRQRY (SEQ ID NO: 17).

9. The method of claim 8, wherein the sequence comprises HGEGTFTSDLSKQMEEEAVRLFIEWLKNGGPSSTRQRY-NH2 (SEQ ID NO: 3).

10. The method of claim 8, wherein the sequence comprises HGEGTFTSDLSKQMEEEAVRLFIEWLRHYLNLVTRQRY-NH2 (SEQ ID NO: 4).

11. The method of claim 8, wherein the sequence comprises IKPEAPREDASPEEENQAYKEFIAYLNLVTRQRY-NH2 (SEQ ID NO: 5).

12. The method of claim 8, wherein the sequence comprises HGEGTFTSDLSKQMEEEAVRLFIEWLKNGGPSSRHYLNLVTRQRY-NH2 (SEQ ID NO: 15).

13. The method of claim 8, wherein the sequence comprises HGEGTFTSDLSKQMEEEAVRLFIEWLKNGGPSSTRQ-NH2 (SEQ ID NO: 16).

14. The method of claim 8, wherein the sequence comprises HGEGTFTSDLSK(azido)QMEEEAVRLFIEWLKNGGPSSTRQRY (SEQ ID NO: 17).

* * * * *

SEQUENCE LISTING

<160> NUMBER OF SEQ ID NOS: 17

<210> SEQ ID NO 1
<211> LENGTH: 34

-continued

<212> TYPE: PRT
<213> ORGANISM: Homo sapiens

<400> SEQUENCE: 1

Ile Lys Pro Glu Ala Pro Arg Glu Asp Ala Ser Pro Glu Glu Leu Asn
1               5                   10                  15

Arg Tyr Tyr Ala Ser Leu Arg His Tyr Leu Asn Leu Val Thr Arg Gln
            20                  25                  30

Arg Tyr

<210> SEQ ID NO 2
<211> LENGTH: 39
<212> TYPE: PRT
<213> ORGANISM: Homo sapiens

<400> SEQUENCE: 2

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 3
<211> LENGTH: 38
<212> TYPE: PRT
<213> ORGANISM: Artificial Sequence
<220> FEATURE:
<223> OTHER INFORMATION: coagonist of GLP-1R and NPYR2

<400> SEQUENCE: 3

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Thr Arg Gln Arg Tyr
        35

<210> SEQ ID NO 4
<211> LENGTH: 38
<212> TYPE: PRT
<213> ORGANISM: Artificial Sequence
<220> FEATURE:
<223> OTHER INFORMATION: coagonist of GLP-1R and NPYR2

<400> SEQUENCE: 4

His Gly Glu Gly Thr Phe Thr Ser Asp Leu Ser Lys Gln Met Glu Glu
1               5                   10                  15

Glu Ala Val Arg Leu Phe Ile Glu Trp Leu Arg His Tyr Leu Asn Leu
            20                  25                  30

Val Thr Arg Gln Arg Tyr
        35

<210> SEQ ID NO 5
<211> LENGTH: 34
<212> TYPE: PRT
<213> ORGANISM: Artificial Sequence
<220> FEATURE:
<223> OTHER INFORMATION: coagonist of GLP-1R and NPYR2

<400> SEQUENCE: 5

Ile Lys Pro Glu Ala Pro Arg Glu Asp Ala Ser Pro Glu Glu Glu Asn

```
1               5                   10                  15
Gln Ala Tyr Lys Glu Phe Ile Ala Tyr Leu Asn Leu Val Thr Arg Gln
            20                  25                  30

Arg Tyr

<210> SEQ ID NO 6
<211> LENGTH: 39
<212> TYPE: PRT
<213> ORGANISM: Artificial Sequence
<220> FEATURE:
<223> OTHER INFORMATION: coagonist of GLP-1R and NPYR2

<400> SEQUENCE: 6

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Thr Arg Gln Arg Tyr
        35

<210> SEQ ID NO 7
<211> LENGTH: 35
<212> TYPE: PRT
<213> ORGANISM: Artificial Sequence
<220> FEATURE:
<223> OTHER INFORMATION: coagonist of GLP-1R and NPYR2

<400> SEQUENCE: 7

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Thr Arg
            20                  25                  30

Gln Arg Tyr
        35

<210> SEQ ID NO 8
<211> LENGTH: 43
<212> TYPE: PRT
<213> ORGANISM: Artificial Sequence
<220> FEATURE:
<223> OTHER INFORMATION: coagonist of GLP-1R and NPYR2

<400> SEQUENCE: 8

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Leu Arg
            20                  25                  30

His Tyr Leu Asn Leu Val Thr Arg Gln Arg Tyr
        35                  40

<210> SEQ ID NO 9
<211> LENGTH: 36
<212> TYPE: PRT
<213> ORGANISM: Artificial Sequence
<220> FEATURE:
<223> OTHER INFORMATION: coagonist of GLP-1R and NPYR2

<400> SEQUENCE: 9

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Thr
            20                  25                  30
```

Arg Gln Arg Tyr
        35

<210> SEQ ID NO 10
<211> LENGTH: 36
<212> TYPE: PRT
<213> ORGANISM: Artificial Sequence
<220> FEATURE:
<223> OTHER INFORMATION: coagonist of GLP-1R and NPYR2

<400> SEQUENCE: 10

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Thr
            20                  25                  30

Arg Gln Arg Tyr
        35

<210> SEQ ID NO 11
<211> LENGTH: 44
<212> TYPE: PRT
<213> ORGANISM: Artificial Sequence
<220> FEATURE:
<223> OTHER INFORMATION: coagonist of GLP-1R and NPYR2

<400> SEQUENCE: 11

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Leu
            20                  25                  30

Arg His Tyr Leu Asn Leu Val Thr Arg Gln Arg Tyr
        35                  40

<210> SEQ ID NO 12
<211> LENGTH: 44
<212> TYPE: PRT
<213> ORGANISM: Artificial Sequence
<220> FEATURE:
<223> OTHER INFORMATION: coagonist of GLP-1R and NPYR2

<400> SEQUENCE: 12

His Gly Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly Leu
            20                  25                  30

Arg His Tyr Leu Asn Leu Val Thr Arg Gln Arg Tyr
        35                  40

<210> SEQ ID NO 13
<211> LENGTH: 44
<212> TYPE: PRT
<213> ORGANISM: Artificial Sequence
<220> FEATURE:
<223> OTHER INFORMATION: coagonist of GLP-1R and NPYR2

<400> SEQUENCE: 13

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Thr Arg Gln Arg Tyr
        35                  40

```
<210> SEQ ID NO 14
<211> LENGTH: 52
<212> TYPE: PRT
<213> ORGANISM: Artificial Sequence
<220> FEATURE:
<223> OTHER INFORMATION: coagonist of GLP-1R and NPYR2

<400> SEQUENCE: 14

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser Leu Arg His Tyr Leu Asn Leu Val Thr
        35                  40                  45

Arg Gln Arg Tyr
    50

<210> SEQ ID NO 15
<211> LENGTH: 45
<212> TYPE: PRT
<213> ORGANISM: Artificial Sequence
<220> FEATURE:
<223> OTHER INFORMATION: coagonist of GLP-1R and NPYR2

<400> SEQUENCE: 15

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Arg His Tyr Leu Asn Leu Val Thr Arg Gln Arg Tyr
        35                  40                  45

<210> SEQ ID NO 16
<211> LENGTH: 36
<212> TYPE: PRT
<213> ORGANISM: Artificial Sequence
<220> FEATURE:
<223> OTHER INFORMATION: coagonist of GLP-1R and NPYR2

<400> SEQUENCE: 16

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Thr Arg Gln
        35

<210> SEQ ID NO 17
<211> LENGTH: 38
<212> TYPE: PRT
<213> ORGANISM: Artificial Sequence
<220> FEATURE:
<223> OTHER INFORMATION: coagonist of GLP-1R and NPYR2

<400> SEQUENCE: 17

His Gly Glu Gly Thr Phe Thr Ser Asp Leu Ser Lys Gln Met Glu Glu
1               5                   10                  15
```

```
Glu Ala Val Arg Leu Phe Ile Glu Trp Leu Lys Asn Gly Gly Pro Ser
            20                  25                  30
Ser Thr Arg Gln Arg Tyr
        35
```